(12) United States Patent
Jahoda et al.

(10) Patent No.: US 6,887,490 B1
(45) Date of Patent: May 3, 2005

(54) GENE THERAPY VEHICLE COMPRISING DERMAL SHEATH TISSUE

(75) Inventors: Amanda Reynolds Jahoda, Richmond (GB); Colin Albert Buchanan Jahoda, 26 Maison Dieu, Richmond, North Yorkshire (GB), DL10 7AU (73) Assignees: Amanda Reynolds-Jahoda, Richmond (GB); Colin Albert Buchanan Jahoda, Richmond (GB)

( * ) Notice: Subject to any disclaimer, the term of this patent is extended or adjusted under 35 U.S.C. 154(b) by 0 days.

(21) Appl. No.: 09/463,174

(22) PCT Filed: Jul. 17, 1998

(86) PCT No.: PCT/GB98/02150

§ 371 (c)(1),
(2), (4) Date: Jan. 18, 2000

(87) PCT Pub. No.: WO99/03505

PCT Pub. Date: Jan. 28, 1999

(30) Foreign Application Priority Data

Jul. 18, 1997 (GB) .............................................. 9715085

(51) Int. Cl.⁷ .......................... A61K 9/10; A61K 35/36; A61L 15/32; C12N 15/85
(52) U.S. Cl. ....................... 424/445; 424/484; 424/447; 424/449; 424/572; 935/10; 935/71; 935/22; 935/59; 935/60; 935/66; 935/70
(58) Field of Search ................................. 424/445, 484, 424/449, 572; 935/70, 71, 22, 59–60, 66

(56) References Cited

U.S. PATENT DOCUMENTS 5,602,309 A * 2/1997 Albers et al.

FOREIGN PATENT DOCUMENTS

| EP | 236014 | 9/1987 |
| EP | 679402 | 4/1995 |
| GB | 2293604 | 4/1996 |
| WO | WO89/02468 | 3/1989 |
| WO | WO93/22430 | 11/1993 |
| WO | WO93/25660 | 12/1993 |
| WO | WO95/01423 | 1/1995 |

OTHER PUBLICATIONS

Jahoda et al., 1992, Development 114:887–97.
Malkinson et al., 1978, Int. J. Dermatol. 17:536–51.
Moll, 1995, J. Investigative Dermatology 105:14–21.
Mulligan, 1993, Science 260:926–32.
Oliver et al., 1989, The dermal papilla and maintenance of hair growth. In The biology of wool and hair. (Ed. G.E. Rogers, P.J. Reis, K.A. Ward, R.C. Marshall), pp. 51–67. Cambridge: Cambridge University Press.
Oliver, 1966, J. Embryol. Exp. Morphol. 16:231–44.
Reynolds et al., 1992, Development 115:587–93.
Reynolds et al., 1991a, Proc. N.Y. Acad. Sci. 624:226–42.
Reynolds et al., 1993, J. Invest Dermatol. 101:634–38.
Haynesworth et al., 1993, Diminution of the number of mesenchymal stem cells a s cause for skeletal ageing. [Eds. J.A. Buckwater & V.M. Goldberg]. pp. 79–87.

* cited by examiner

Primary Examiner—Edward J. Webman
(74) Attorney, Agent, or Firm—Klauber & Jackson (57) ABSTRACT

The invention herein described relates to a gene therapy vehicle, comprising dermal sheath tissue and/or cells derived from portions of hair follicles which show pluripotentiality, and which has use in the delivery of therapeutic agents to selected tissues and advantageously has the potential to repair/replace damaged tissue.

33 Claims, 11 Drawing Sheets

FIG. 14 eGFP gene removed via cutting with HindIII (41) and NotI (820)

GENE THERAPY VEHICLE COMPRISING DERMAL SHEATH TISSUE

The invention relates to the use of dermal sheath tissue and/or cells derived therefrom and/or portions of hair follicles containing these and other cell populations for use particularly, but not exclusively in gene therapy/vaccine development.

Human gene therapy vectors constructed to date are typically derived from viruses (1). The rationale being that such vectors can easily penetrate cells by virtue of naturally infecting human cells and so can incorporate fragments of foreign DNA into a target cell population. The most widely investigated viruses are of the adenovirus, retrovirus, parvovirus and herpesvirus families. With the exception of retroviruses, all have been derived from viruses originally isolated from humans. In nearly every case the vectors used in both ex and in vivo work have been derived from virus mutants originally created to study gene function, rather than to act as gene delivery systems.

Although adenoviruses have proved to be popular because of ease of growth of stocks to high titre, they have many associated problems. For example it is known that viruses which are replication incompetent in cell culture have caused tissue damage and respiratory disease in patients treated with such vectors (2).

Herpesvirus vector development to date has concentrated on derivatives of the common human pathogen herpes simplex virus (HSV). The advantage of using this virus is that it is the most intensively studied of all the herpesviruses. The sequence of the virus genome has been determined, there is a wide range of well characterised virus mutants available and transcriptional control processes are well understood. However the disadvantage with this virus is that the mutant virus is difficult to produce as high titre stocks and in some cases has an unacceptable reversion frequency. Additionally, it is a likely problem with HSV vectors that there is an innate immune response present in the majority of the population; it is predicted that HSV vectors will suffer the same problem as those derived from human adenoviruses, when delivered to an immunologically competent site.

Additionally, and more recently, naturally occurring specific cell populations have been investigated as gene therapy delivery systems however such systems have to date only employed self-derived cells and consequently are limited to the disease state of the individual from which the cells are derived. Such systems suffer from immunological repercussions and have not produced particularly encouraging results nor do they offer the possibility of inter and/or intra species therapies.

Thus a vehicle capable of efficient and immunopriviledged gene delivery to human cells would have a wide range of uses in human gene therapy, for example delivery of a correct copy of human tumour suppressor genes to tumours of a variety of different organs and/or as a vaccine delivery vehicle to induce specific immunity.

Skin is a highly complex organ covering the external surface of the body and merging, at various body openings, with the mucous membranes of the alimentary and other canals. It has multiple functions such as preventing water loss from the body, but predominantly acts as a protective barrier against the action of physical, chemical and bacterial agents on deeper tissues. Skin is elastic and except for a few areas such as the palms, soles and ears it is loosely attached to underlying tissue. It varies in thickness from 0.5 mm (0.02 inches) on the eyelids to 4 mm (0.17 inches) or more on the palms and soles.

Skin is composed of two layers (please refer to FIG. 1 which illustrates an anatomical cross-sectional view through a slice of skin), the outer layer, which is comparatively thin (0.1 mm) is called the epidermis, or cuticle, it is several cells thick and has an external, horny layer of dead cells that are constantly shed from the surface and replaced from below by a basal layer of cells, called the stratum germinativum. The epidermis is composed predominantly of keratinocytes which make up over 95% of the cell population, the rest include dendritic cells such as Langerhans cells and melanocytes. It is essentially cellular and non-vascular, there being relatively little extracellular matrix except for the layer of collagen and other proteins beneath the basal layer of keratinocytes. Keratinocytes of the basal layer are constantly dividing, and daughter cells subsequently move outwards, where they undergo a period of differentiation and are eventually sloughed off from the surface. The inner layer of the skin is called the dermis and is composed of a network of collagenous extracellular material, elastic fibres, blood vessels and nerves. Contained within it are hair follicles with associated sebaceous glands (collectively known as the pilosebaceous unit) and sweat glands. The interface between the epidermis and dermis is extremely irregular and consists of a succession of interdigitations, or finger like projections. Beneath the basal epidermal cells along this interface the specialised extracellular matrix is organised into a distinct structure called the basement membrane.

The mammalian hair fibre is the product of a small but complex, cylindrical arrangement of tissues known as the hair follicle. Follicles lie angularly underneath the skin's surface, their distal most epidermis being in direct continuation with that of the skin at the point where they open externally. Although small, the follicle comprises a highly organised system of recognisably different layers arranged in concentric series. Active hair follicles extend down through the dermis, the hypodermis (a loose layer of connective tissue), and the fat or adipose layer.

Figure 1:
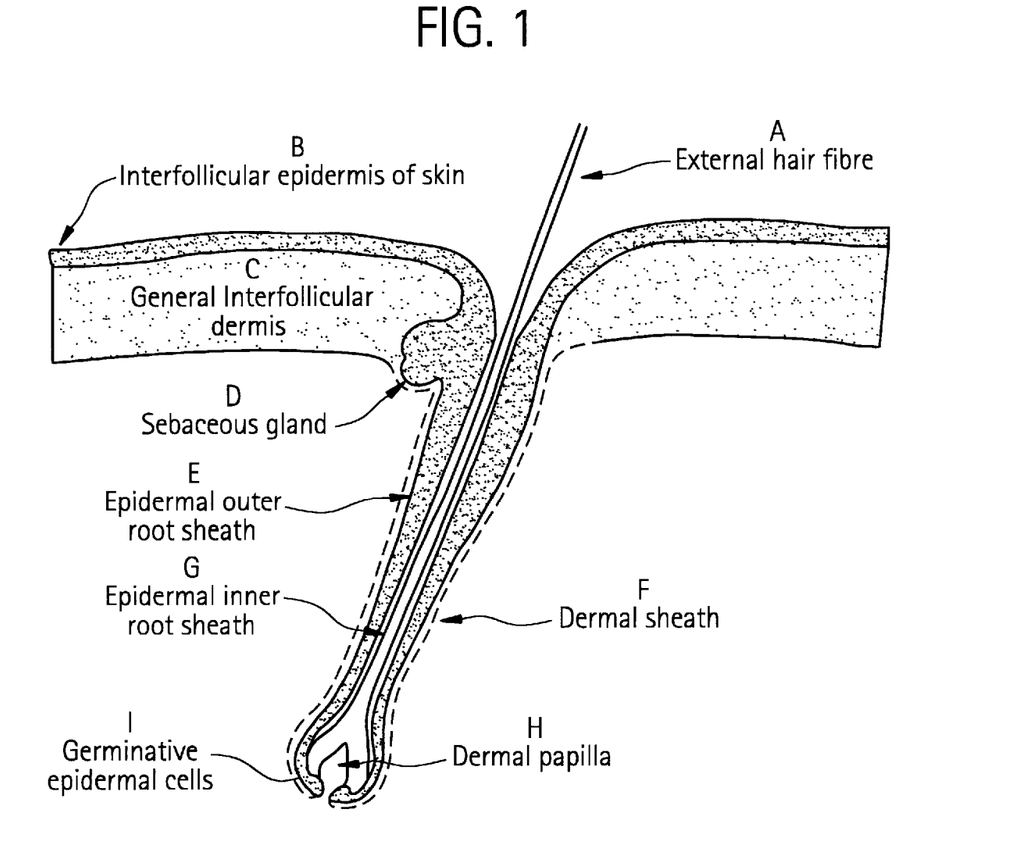
FIG. 1 represents a diagrammatic illustration of an anatomical cross-sectional view through a slide of skin.

At the base of any active follicle lies the hair bulb, which consists of a body of dermal cells, known as the dermal papilla, contained in an inverted cup of epidermal cells known as the epidermal matrix (please refer to FIG. 1). Irrespective of follicle type, the hair fibre, together with several supportive epidermal layers, is produced by germinative epidermal cells at the very base of this epidermal matrix. The lowermost dermal sheath is contiguous with the papilla basal stalk, from where it curves externally around all of the epidermal layers of hair matrix as a thin covering of tissue, and then continues as a tube or sleeve for the length of the follicle. The dermal sheath is otherwise known as the connective tissue sheath.

Developing skin appendages such as feather and hair follicles rely on interaction between the skin's two layers, the epidermis and the dermis. In embryonic development, a sequential exchange of information between these layers underpins a complex series of morphogenetic processes culminating in the formation of adult follicle structures. However, following maturity, and in contrast to general skin dermal and epidermal cells, certain hair follicle cell populations retain embryonic-type inductive, interactive and biosynthetic behaviours. These properties are likely to derive from the very dynamic nature of the cyclically productive follicle, in which repeated tissue remodelling necessitates a high level of dermal-epidermal interactive communication, as is vital for embryonic development and, as would be desirable in any form of tissue reconstruction.

Hair fibre is produced at the base of an active follicle at a very rapid rate (0.4 mm per day in the human scalp follicles and up to 1.5 mm per day in the rat vibrissa or whiskers), which means that cell proliferation in the follicle epidermis ranks amongst the fastest in adult tissues (3).

The most dynamic region of the hair follicle is the deeply embedded end bulb, where local dermal-epidermal interactions drive active fibre growth. This same region is also central to the developmental changes and tissue remodelling involved in the hair fibre's or appendages precise alternation between growth and regression phases. As a key player in the activities, the dermal papilla appears to orchestrate the complex program of differentiation that characterises hair fibre formation from the primative germinative epidermal cell source (4–7). The lowermost dermal sheath initiates below the papilla basal stalk, from where it curves outwards and upwards to externally enclose all of the layers of the epidermal hair matrix as a thin cup of tissue. (Please refer to FIG. 1). The dermal sheath continues as a tubular arrangement for the length of the follicle, as does the epidermal outer root sheath which lies immediately internal to it in between the two layers is a specialised basement membrane termed the glassy membrane. The outer root sheath constitutes little more than an epidermal monolayer in the lower follicle, but becomes increasingly thickened more superficially.

Whilst the individual anatomical components and cell sub-populations of skin are well established their intra/inter biochemical interactions and control mechanism remains largely a matter for speculation and intense research.

The most important of all cells types are those at the source of every biological system ie stem cells, since they vitally sustain and replenish the more differentiated descendent population and as they become specialised develop a characteristic function. Yet these are the cells which are least understood in terms of their distribution, behaviour and the actors by which they may be defined. The ability to provide significant numbers of pure, unstimulated, undifferentiated, primitive stem cells from an adult organ would be likely to have a broad impact on our fundamental understanding of cell biology, and would yield positive and promising approaches to future therapeutic advances.

Serendipitously, we have studied hair follicles and identified a specific cell population with immunoprivilege and stem specific cell potential that can be used most advantageously as a cellular delivery system in gene therapy.

We have found that the implantation of male follicle-derived dermal sheath cells into a female recipient does not lead to the typical immune response and subsequent rejection that one would expect. The same observation held true even after a subsequent set of implantations with the same human host and donor, when second set rejection would have been predicted. Such results show that dermal sheath cells have some form of privileged immune status. A number of our tissue interaction/induction studies have also clearly demonstrated that cells derived from different species appendages are very capable of interacting with each other, and communicating at the appropriate levels to allow complex morphogenesis. This being the case, dermal sheath tissue and/or cells derived therefrom represent a cell population of major consequence in gene therapy as vehicles for both inter and intra species therapy delivery. Additionally the ability of dermal sheath tissue and/or cells derived therefrom to differentiate into a variety of different phenotypes makes their contribution to gene therapy even more significant, in that using such cells as vehicles means that not only would they be tolerated in multiple and different tissue/cell sites, but that they would also be more effective and penetrating by differentiating into multiple tissue types depending on the site of delivery. Further natural attributes that pre-dispose follicle cells as candidates for the application of gene therapy include: their similarity to wound myofibroblasts; their exhibition of stem cell-type qualities including those characterising primative muscle lineages, indeed follicle-derived muscle stem cells are especially suited to gene therapy applications because of their ability to fuse with other cells. Furthermore since dermal sheath cells have many of the properties of smooth muscle cells they have an additional potential in vascular related therapy by incorporation into blood vessels as the smooth muscle component; production of a unique embryonic-type extracellular matrix and, the fact that they exhibit impressive regenerative and inductive abilities.

It is therefore an object of the invention to provide a new gene therapy system that employs follicle derived cells/tissues and/or their attributes.

It is a yet further object of the invention to provide an inter or intra species gene therapy that employs follicle derived cells/tissues and/or their attributes.

It is a yet further object of the invention to provide a gene therapy vehicle having multi-potential incorporation and differentiation properties.

According to a first aspect of the invention there is provided dermal sheath tissue and/or cells derived therefrom and/or cells typically closely associated with hair follicles for use in a gene therapy.

According to a further aspect of the invention there is provided a gene therapy vehicle for delivering at least one selected gene, or functional fragment thereof to a target site comprising dermal sheath tissue and/or cells derived therefrom and/or cells typically closely associated with hair follicles.

Reference herein to a functional fragment thereof is intended to include a part of a gene that provides for the expression of the corresponding protein or an active or effective part thereof.

Reference herein to cells typically closely associated with hair follicles is intended to include cells that are functionally and/or locationally associated with and/or within hair follicles.

In a preferred embodiment of the invention said dermal sheath tissue and/or said cells derived therefrom and/or said cells typically closely associated with hair follicles is/are derived from a selected portion of a follicle ideally the lower third thereof and even more ideally are derived from a segment or ring of a combination of follicle tissue/cells.

In a yet further preferred embodiment of the invention said gene therapy vehicle is suitably engineered, ideally using recombinant techniques, so as to include at least one insertion site into which at least one selected gene can be placed. Those skilled in the art will appreciate that the provision of this insertion site allows the gene therapy vehicle to carry a selected gene to a desired location. More preferably still said selected gene is functionally inserted into said gene therapy vehicle so that the expression of said gene results in the provision of the corresponding protein product. It would be understood by those skilled in the art that the nature of the gene to be inserted will be selected having regard to the purpose of the gene therapy vehicle and thus the nature of the condition to be cured, treated or alleviated. In addition, said gene therapy vehicle may be provided with multiple insertion sites with a view to carrying multiple genes and so providing for the delivery of multiple proteins, either of a similar or different nature. In each instance, said selected gene for insertion is arranged so as to be inserted in-frame with the genome of the gene therapy vehicle so as to provide for correct expression of same.

In a yet further preferred embodiment of the invention said gene therapy vehicle comprises at least one selected gene or functional fragment thereof which is operationally attached to a regulatable or inducible or a constitutive promoter.

In a yet further aspect of the invention there is provided a vector for transforming or transfecting the gene therapy vehicle of the invention wherein said vector is provided with at least one insertion site into which at least one selected gene can be placed and also other expression control elements for ensuing that once the vector infects or penetrates said tissue and/or cells derived therefrom expression of the said selected gene can take place.

In a yet further preferred embodiment of the invention there is provided a therapeutic composition comprising a suitable carrier for the gene therapy vehicle in accordance with the invention, ideally said carrier can be formulated to have anti-bacterial properties and/or anti-septic properties and more ideally further include growth promoting additives and/or local anaesthetics. Ideally said therapeutic composition may be adapted to be applied topically in the form of dermal sheath cells suspended in a suitable carrier solution/gel/cream/emollient; alternatively said composition may be adapted to be administered by injection and so comprise a carrier solution; alternatively still, said carrier may be incorporated and/or embedded therein and/or associated therewith and/or attached thereto a plaster or bandage or the like.

According to a further aspect of the invention there is provided a potential gene therapy vehicle for use in delivering a selected gene, or functional fragment thereof, to a given site wherein said gene therapy vehicle comprises dermal sheath tissue and/or cells derived therefrom and/or cells typically closely associated with hair follicles which cells and/or tissue that have been suitably adapted to accommodate heterologous genetic material and which, in vivo, have the capacity to selectively differentiate to provide at least one differentiated tissue type.

It will be apparent to those skilled in the art that, given the pluripotentiality of these cells, that the site of implantation will, to some extent, determine the differentiated pathway along which these cells will develop. Thus, the site of implantation will determine the nature of the phenotype of these cells and therefore one is provided with a gene therapy vehicle that not only is able to deliver at least one selected gene but which also has the added advantage of being able to provide differentiated tissue. This feature is particularly important where an individual may have suffered tissue damage, for example, following wounding of any type or following ischemia or vascular damage, or even removal of at least part of an organ or tissue.

It would therefore be seen that, advantageously, the gene therapy vehicle of the invention may be suitably cultured for the purpose of implantation and/or suitably impregnated onto wound healing materials such as bandages or seeded into biomaterials or coated onto replacement blood vessels or the like.

In the instance where the gene therapy vehicle is to be used in relation to wound healing said dermal sheath tissue and/or said cells derived therefrom and/or cells typically closely associated with hair follicles are provided or combined with at least one other appropriate cell type from a hair follicle. This combination is favoured because our experiments have shown that dermal papilla tissue, or cells derived therefrom may assist in the closure of wound and in the reduction of scar tissue.

In a yet further preferred embodiment of the invention there is provided a wound healing system comprising a suitable matrix material having incorporated and/or embedded therein and/or associated therewith and/or attached thereto a gene therapy vehicle in accordance with the invention, ideally said matrix material comprises native collagen or collagenous gels or lattices constructed from reconstituted collagen or highly complex mixtures of reconstructed collagen and a multitude of extracellular matrix products or any other suitable matrix material known to those skilled in the art, the selection of which is not intended to limit the scope of the invention.

In a yet further preferred embodiment of the invention there is provided a surgical dressing comprising a web material and a suitable matrix material, at least one of which materials has incorporated and/or embedded therein and/or associated therewith and/or attached thereto a gene therapy vehicle in accordance with the invention, ideally said surgical dressing is conventional, the selection of which is not intended to limit the scope of the invention.

According to a yet further aspect of the invention there is provided a wound healing system as hereinbefore described for use in treatment of acute and/or chronic and/or minor and/or severe wound healing; and/or cartilage repair and/or bone repair and/or muscle repair and/or connective tissue repair and/or blood vessel repair.

In summary, we believe the dermal sheath tissue and/or cells derived therefrom and/or cells typically closely associated with hair follicles have an important part to play in gene therapy because this tissue and/or cells derived therefrom and/or cells typically closely associated with hair follicles:

i) exhibit immunoprivilege,
ii) exhibit the capacity to incorporate themselves within disturbed tissue sites and fuse directly with host cells,
iii) exhibit multipotentiality in terms of the differentiated cell lineages they can follow,
iv) exhibit interactive flexibility both in terms of merging within different body sites and also surviving and interacting within different species,
v) exhibit longevity and general durability, e.g. can be stored long term at low temperatures and still retain the aforementioned properties,
vi) advantageously are of adult origin and since most gene therapies will be aimed at adults the gene therapy of the invention provides the benefits of embryonic-type properties without the potential risk of utilising genuine embryo derived cells,
vii) represent a relatively rich deposit of stem cells,
viii) promote healing thereby reducing scarring and delay fibro-fatty deposit accumulation,
ix) have the ability to pass through the basement membrane, by virtue of the production of large amounts of metalloproteinases, as seen in lower follicle regeneration when sheath cells move through basement membranes on the way to becoming papilla cells (8, 9), thus these cells have the potential to reach parts of the body remote from site of delivery.

Thus the invention presents a gene therapy delivery system that can be reliably manufactured and then stored for future use. Additionally, this tissue and/or cells derived therefrom can exist for a long time in culture under extreme stress, and accordingly presents a gene therapy delivery system that is robust in nature, another favourable advantage in terms of storage, and subsequent application.

An embodiment of the invention will now be described by way of example only with reference to the following Figures wherein:

A external hair fibre;
B interfollicular epidermis of skin;
C general interfollicular dermis;
D sebaceous glad;
E epidermal outer root sheath (shown in solid black);
F dermal sheath (broken line l);
G epidermal inner root sheath (thin layer around fibre);
H dermal papilla (central pear shape);
I germinative epidermal cells (form a tight collar around papillar base).

FIG. 2 represents a diagrammatic representation of procedures;
A. male scalp
A1 heals and upper follicle portions regenerate to restore pre-biopsy state
B. punch biopsy taken
B1. Punch biopsy replaced on scalp
C. end bulbs amputated
D. end bulbs dissected
E. to provide various tissue components
F. isolated papilla
G. isolated sheath
H. pooled dermal papillae
I. pooled dermal sheath
J. sheath and papillae transplanted into female forearm skin
K. female arm where male tissue has induced hair follicle neogenesis!

as shown in FIG. 2e, marked by a star (*).

FIG. 12 represents pictorial evidence of dermal sheath cell capability to differentiate into different mesenchymal cells.
(A) Long tern cultured (over a year) human dermal sheath cells
(B) Dermal sheath cells appearing to fuse in myoblast (muscle-lil)
(C) Myotube-like structures in dermal sheath cell cultures.
(D) Adipocyte (fit producing) cells.
(E) Chondrocyte (cartilage-type) cells.
(F) Mineral producing bone precursor cells—Von Kossa stained.
(G) Dermal sheath cells labelled immunohistochemically for alpha-smooth muscle actin.
(H) Human dermal sheath cells positively stained for smooth muscle myosin.
(I) Dermal sheath cells labelled positively for desmin.

EXPERIMENTAL APPROACH

Tissue Isolation

Figure 2:
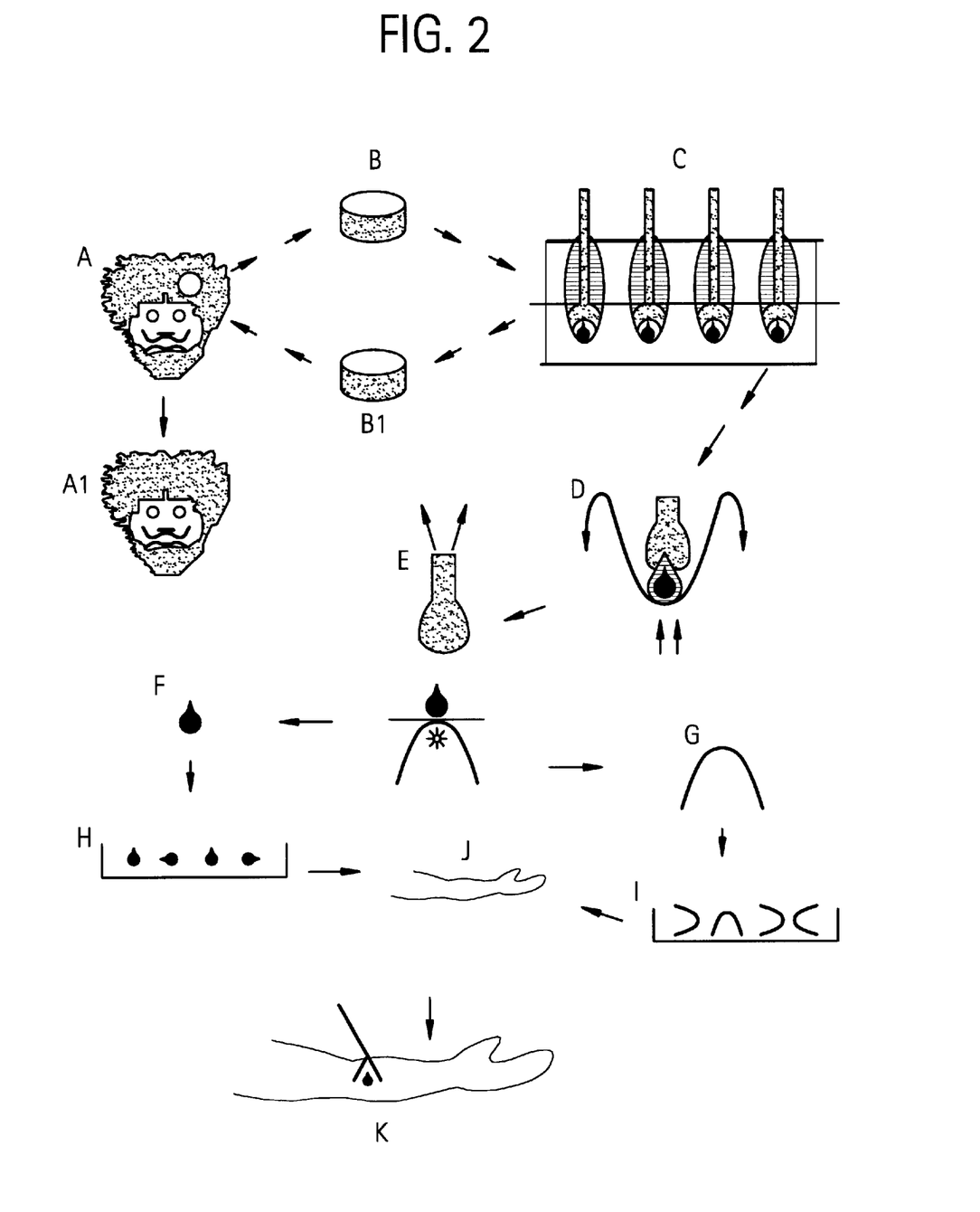

A small patch of male scalp skin (about 1.5 $cm^2$) was coarsely shaven, leaving some fibre still exposed to allow for subsequent plucking. The area was wiped with an antiseptic solution and injected locally with lignocaine plus adrenaline anaesthesia, before taking a 6 mm diameter punch biopsy at an angle appropriate to follicle orientation. The most proximal tips (under ⅛th of length) of the exposed follicles were amputated under a dissecting microscope (Zeiss) from the inverted biopsy, and transferred to individual drops of minimal essential medium (Gibco) at 4° C. After plucking the hair fibres from the transected follicles, the biopsy was returned to its original scalp skin site and left to heal. This initial procedure lasted about 20–25 mins. Refer to FIG. 2 (a, a1, b, b1 and c) which represents a diagrammatic representation of procedures.

Figure 3:
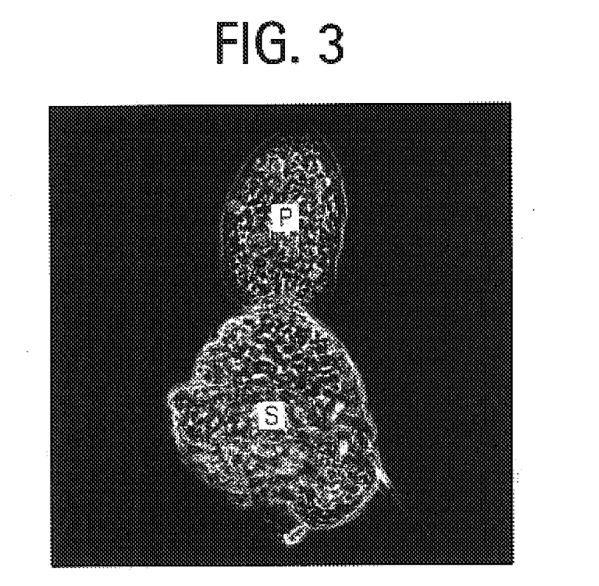
FIG. 3 represents pictorial evidence of isolated dermal papilla (P) and sheath (S) tissue microdissected from male scalp hair follicle end bulbs.

The outermost end bulb dermal layers were inverted to allow the epidermal matrix (including undifferentiated issue) to be scraped away and discarded (FIG. 2d). Dermal papillae, isolated by basal stalk severance (FIG. 2e), were pooled in fresh medium (FIG. 2h). The thin external covering of connective tissue was then teased from the pieces of sheath dermis before they were similarly pooled in fresh medium. (FIGS. 2g and i). FIG. 3 represents pictorial evidence of isolated dermal papilla (P) and sheath (S) tissue microdissected from male scalp hair follicle end bulbs as shown in FIG. 2e marked by a star (*).

Implantations

These operations were so minimally invasive as to be practically imperceivable, hence, no form of local anaesthetic pretreatment was deemed necessary. This also avoided the possibility that the anaesthetic might adversely affect the tiny quantities of vulnerable dermis that were to be implanted.

A small, shallow wound was made in the inner forearm of the female recipient with the point of a scalpel blade, and; widened slightly using the tips of very fine (No.5) watchmakers forceps (FIG. 2j). In the few instances when a tiny amount of blood or fluid was exuded, it was absorbed using tiny sterile cotton wool balls. Two sets of operations were performed.

Figure 4:
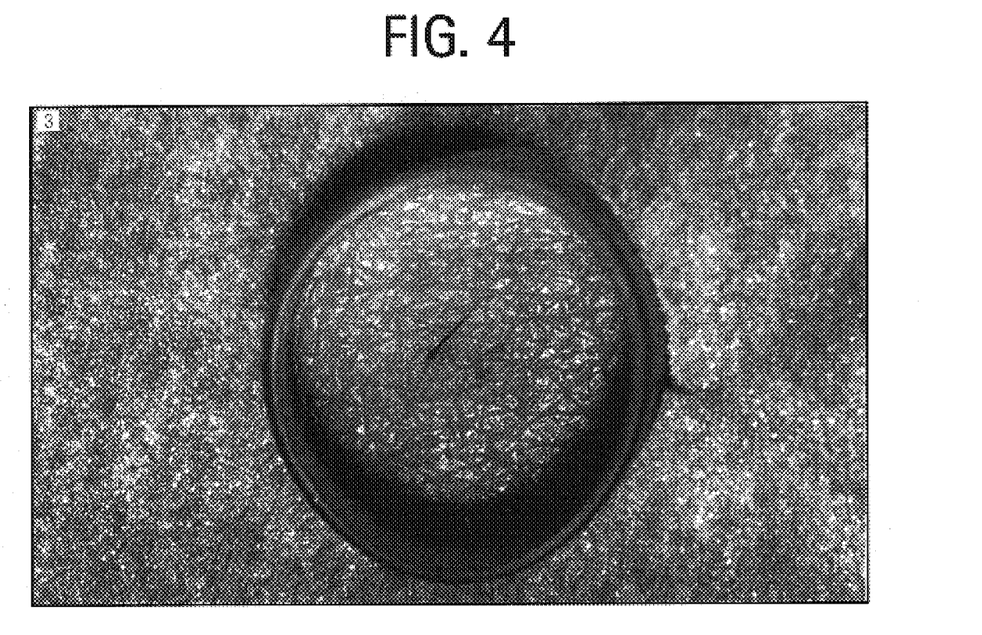
FIG. 4 represents pictorial evidence of two hair fibres which have been produced in the immediate vicinity of the male dermal sheath-implanted female skin wound protected by a small silicone rubber collar.
Figure 5:
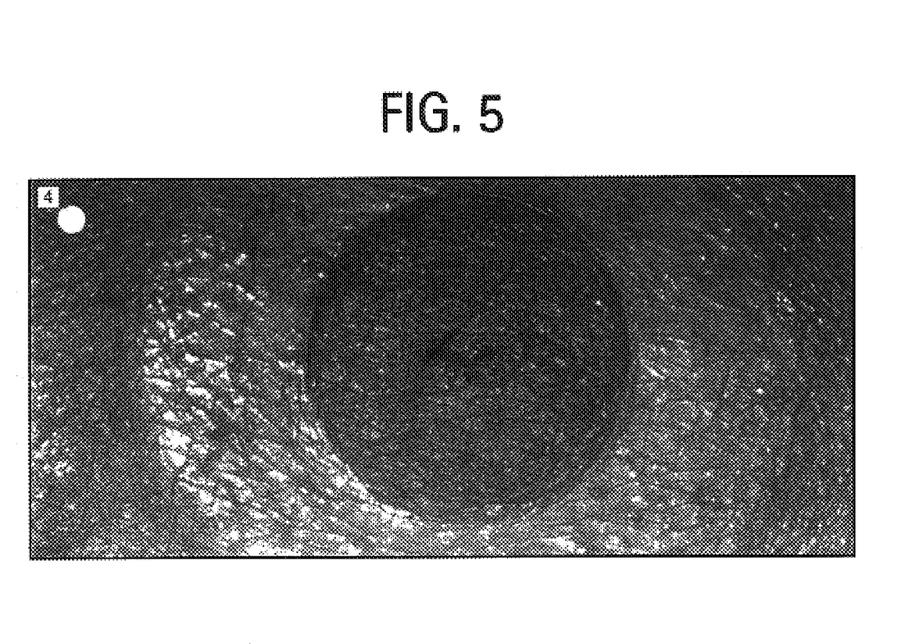
FIG. 5 represents pictorial evidence of FIG. 4 after the silicone collar (and plaster attachment) has been removed.

In the first, dermal sheath tissue from twelve follicles were implanted into two wound sites (six in each), approximately 10 hours after the end bulbs had been removed from the biopsy. The second, involved the implantation of 11 pieces of dermal sheath into one wound site, 9 dermal papillae into a second, and 2 papillae (which stuck to the forceps and had to be re-implanted separately) into a third, about 20 hours after biopsy. In all cases, the material was collected in as little fluid as possible and then transferred directly to the wound site, so that it could be rapidly inserted into the skin on the end of the forceps. The wounds were initially left untreated and uncovered. When hair fibres were seen emerging from the implanted sites (3–4 weeks later), small silicone rings with rims were placed over them and secured using surgical tape—as a cautionary measure to protect against abrasion, please refer to FIG. 4 which represents pictorial evidence of two hair fibres which have been produced in the immediate vicinity of the male dermal sheath-implanted female skin wound protected by a small silicone rubber collar and FIG. 5 which represents pictorial evidence of FIG. 4 after the silicon collar (and plaster attachment) have been removed.

The first set of two wound sites were biopsied together as a single piece of elliptical skin, 77 days after sheath tissue implantation, and were fixed immediately in freshly prepared 4% paraformaldehyde at pH 7.3. The second set of wounds (made 3 months after the first) were treated similarly—being removed 42 days post operatively as two small (4 mm) punch biopsies (more precisely located by their positioning next to moles). Detailed external observations and photographic recordings of the male donor scalp, and recipient female arm skin sites, were made at regular intervals.

Fluorophore-Labelled Y-Chromosome Probe [Imagenetics]

The spectrum green fluorophore-labelled enumerator probe (Imagenetics), consisted of chromosome-specific sequences from highly repeated human satellite DNAs. The target DNA in the tissue sections was denatured in 70% formamide/2×SSC at 70° C. for 10 mins. Meanwhile, the probe mixture was prepared to contain: 7 $\mu$l SpectrumCEP hybridisation buffer (dextran sulphate, formamide, SSC, pH 7.0), 1 $\mu$l SpectrumCEP probe (fluorophore-labelled enumerator probe and blocking DNA in Tris-EDTA buffer) and 2 $\mu$l of 5× blocking solution (× number of slides), which were centrifuged (1–secs), heated for 5 mins in a 75° C. water bath and then placed on ice. The denatured slides were washed in 70%, 85% and 100% ethanol (1 min in each) and then air dried. Each slide, heated to 45° C., received 10 $\mu$l of probe mix and then a silanised coverslip which was sealed at the edges prior to the slides incubation in a humid box at 42° C. for 18 hours. Following hybridisation and coverslip removal, the slides were washed for: 3×10 mins in 50% formamide/2×SSC; 10 mins in 2×SSC, and 5 mins in 2×SSC/0.1% NP-40, all containing Denhardts solution, 50 $\mu$g/ml sonicated salmon sperm DNA, 1% milk powder and 0.1% Tween-20 and all at 45° C. The slides were allowed to air dry in the dark, and then 10 $\mu$l of propidium iodide counterstain (Imagenetics) and a coverslip, added to each Digoxigenin-Labelled Y-Chromosome Probe [Boehringer Mannheim]

Each slide received 20 $\mu$l of the hybridisation mixture, consisting of: 10 $\mu$l formamide [50% of final volume]; 5 $\mu$l 4× hybridisation solution; 2.5 $\mu$l probe [50 ng]; 2.5 $\mu$l 8× blocking solutions. The mixture was covered by a silanised glass coverslip, sealed and then denatured for 5->10 mins at 72° C. on a pre-warmed glass plate in the oven, before incubation in a moist chamber at 37° C. overnight. The slides were washed for 3×5 mins in 2×SSC, prior to 30 mins in 50 ml TBS containing 1× blocking solution (as above) and 1% Boehringer kit blocker reagent—both also at 37° C. To promote detection, the slides were transferred to 50 ml TBS and 50 $\mu$l anti-digoxigenin alkaline phosphatase conjugate [200 $\mu$g/ml] containing 1% kit blocker reagent for 30 mins at 37° C., and then were washed for 3×10 mins in 0.2% Tween 20 in TBS at room temperature. Immediately before use, 4.5 $\mu$l of NBT, 3.5 $\mu$l of X-phosphate and 0.24 mg of levamisole (Sigma) was added to 1 ml of Tris/NaCl/MgCl$_2$ buffer. Appropriate volumes for the number and size of the sections were added and the slides incubated at room temperature in a humidified box covered in foil until the dark blue/purple colour developed. To stop the reaction, the slides were rinsed for 5 mins at room temperature in 10 mM Tris-Cl/1 mM Na2 EDTA, pH 8.0.

Sections to be counter stained with propidium iodide were incubated for 5 mins at room temperature in the dark in 50 ml TBS+5 ul propidium iodide [1 mg/ml], or a similar concentration of acriflavine yellow, washed for 2–3 mins under running water, and then allowed to air dry in the dark. Finally, the sections were mounted in 20 $\mu$l of anti-fading solution under a glass coverslip, which was sealed at the edges with nail varnish Transfection of Dermal Sheath Cells Cultured from Rat Vibrissa Follicles Rat dermal sheath cells cultured from vibrissa follicles were transfected using lipofectamine, according to the following procedure. 1–3×10$^5$ cells were seeded per well in 2 ml of the appropriate complete growth media and plated into a six-well or 35-mm tissue culture plate. The cells were then incubated at 37° C. in a CO$_2$ incubator until the cells were 50–80% confluent. This procedure usually lasted 18 to 24 hours. The following solutions were prepared for each transfection, solution A contained dilute 1–2 g of DNA into 100 $\mu$g serum free medium, typically OPTI-MEM® reduced serum medium (GIBCO BRL CAT.NO.31985). Solution B contained for each transfection, dilute 2–25 $\mu$l of lipofectamine reagent into 100 $\mu$l of serum free medium. Subsequently the solutions A and B were mixed gently and incubated at room temperature for 15 to 45 minutes so as to allow the DNA liposome complexes to form. Further serum-free medium was added to each tube containing the complexes, and cells were incubated with complexes for 2 to 24 hours at 37° C. in a CO$_2$ incubator. Following incubation, 1 ml of growth medium containing twice the normal concentration of serum was added without removing the transfection mixture. The medium was replaced with fresh complete medium at 18 to 24 hours following start of transfection. Cells were active for gene activity 24 to 42 hours after the start of transfection.

Insertion of eGFP Gene into the Vector

Figure 14:
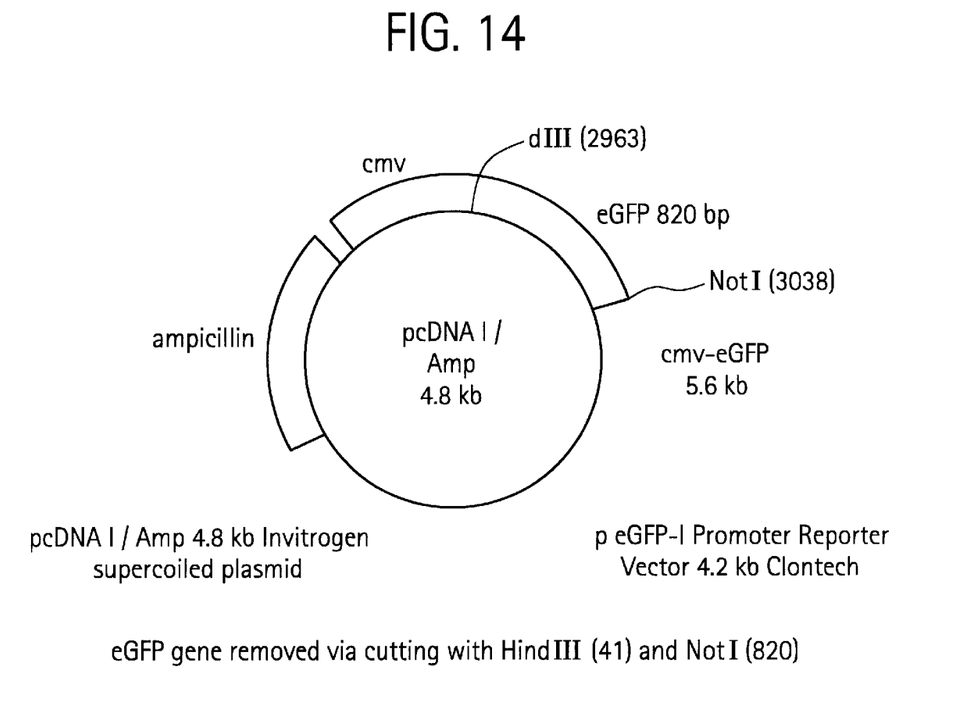
FIG. 14 represents a schematic representation of an e-GFP construct for transforming dermal sheath cells.
Figure 15:
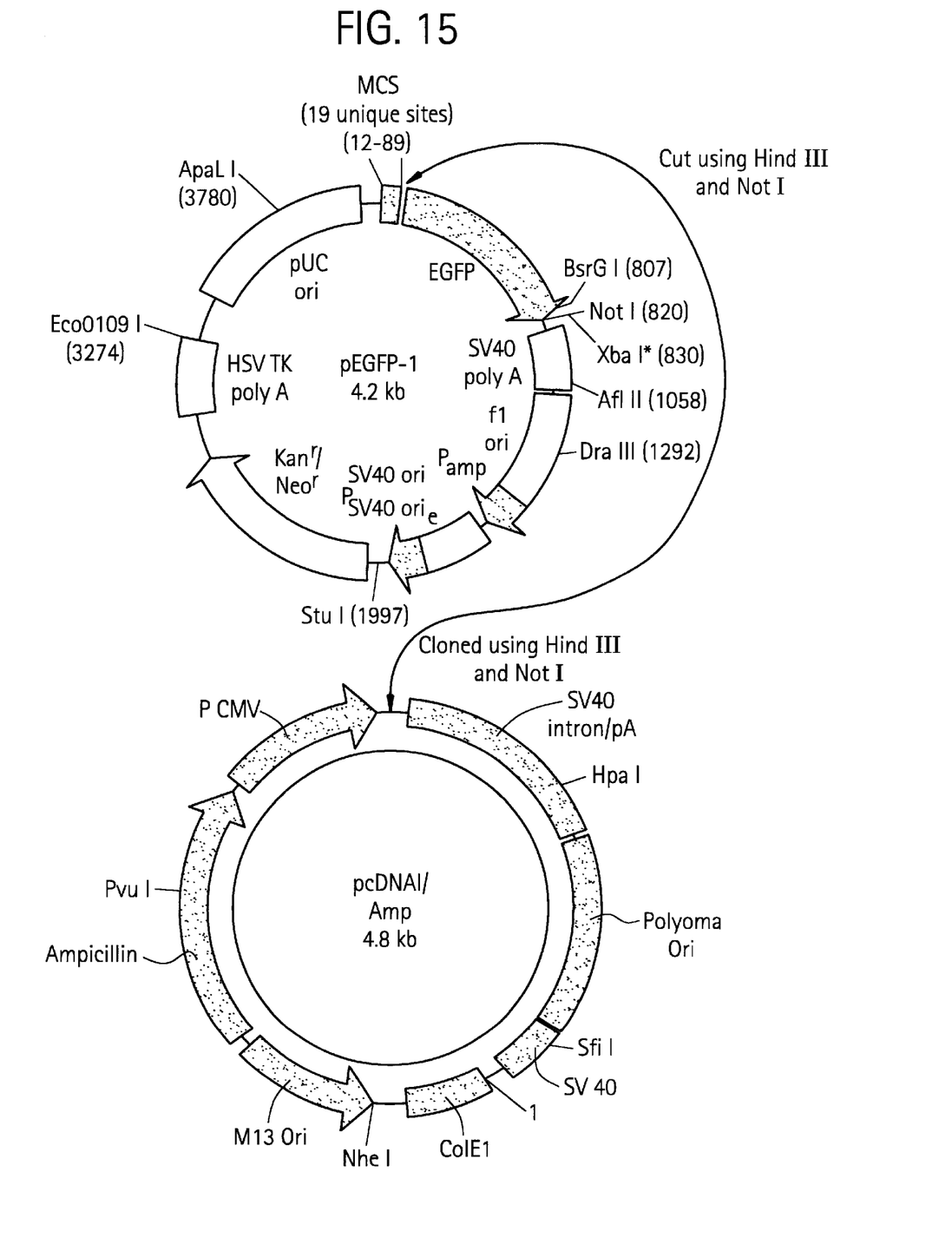
FIG. 15 represents a schematic representation of a method for inserting the e-GFP gene into a vector.
Figure 16A:
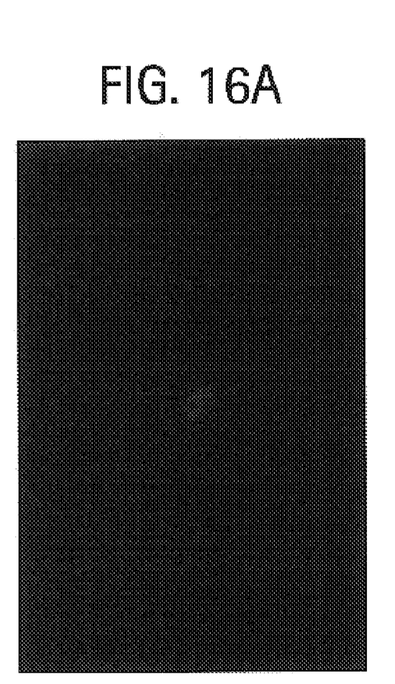
FIG. 16 represents pictorial evidence of transfected dermal sheath cells with a construct containing enhanced green fluorescent protein e-GFP and a constitutive promoter.
Figure 16B:
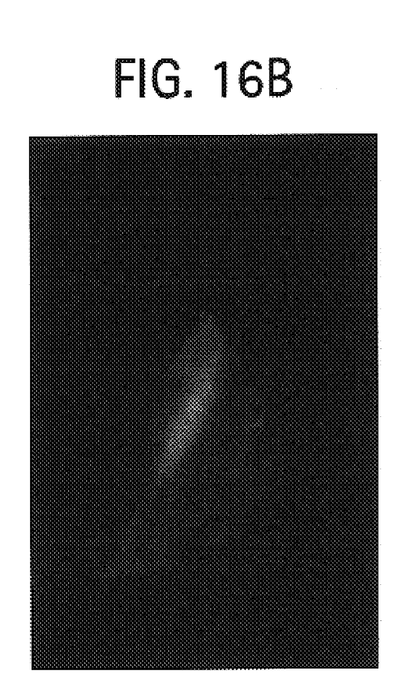
Figure 16C:
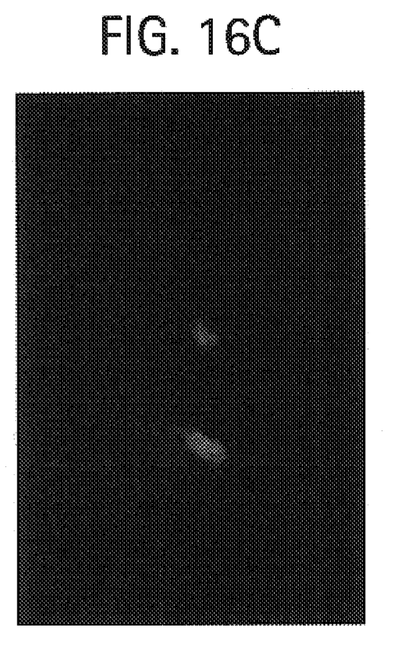
Figure 16D:
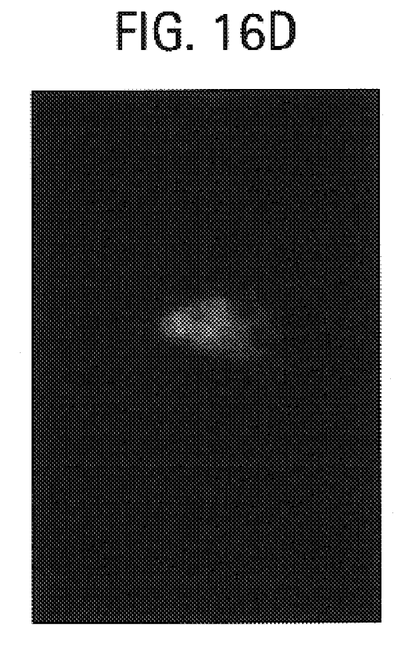

The eGFP gene was cut out of the Clontech vector (GenBank Accession number U55761, Catalog number 6086-1) using Hind III and Not I at the multiple binding site region (FIG. 15). The eGFP gene was then cloned into the Invitrogen vector (pc DNA1/Amp; 4.8 kb) at the site just after the P cmv consitutative promoter using Hind III and Not I in accordance with the method as outlined in FIG. 15, so that the final construct is as per represented in FIG. 14.

Storage of Dermal Sheath Tissue

Cold temperature storage of dermal sheath tissue/cells; additionally their subjection to adverse conditions to highlight stem cell-type characteristics—including capacity for preferential survival.

Human skin samples (as detailed directly above) were cleaned and appropriately microdissected to provide: (a) 3 mm$^2$ portions of whole skin; (b) isolated hair follicles; (c) fragments of glassy membrane sandwiched between thin layers of sheath dermis and ORS epidermis, and (d) primary cultures of dermal sheath cells (prepared as above). Each of these four levels of tissue complexity were then subjected to six different forms of adverse conditions (each repeated with and without serum, and/or, glucose and glycerol): (i) prolonged cold temperate storage at 4° C.; (ii) repeated freeze/ thaw cycles at −20° C.; (iii) repeated freeze/thaw storage at −80° C. in DMSO;

Results

Sheath Implants

All of the sites that had been implanted with dermal sheath tissue healed rapidly and in a manner that seemed typical of any superficial skin lesion. Fine narrow scabs formed as the site dried and then were lost over the next few days to leave a very flint wound, which was almost imperceivable by about the 10th day. There was no external sign of any inflammatory reaction in or around the wounds, nor any physical perception of the site. The tip of a fibre that was darker and disproportionately sturdier for its length than any of the arm skins local vellus hairs, was first noticed on the 24th day after the dermal sheath had been introduced. On the 33rd day post-implantation, a second much finer and unpigmented fibre was seen to have emerged just to the side of the first. A very light peppering of pigmented material was also visible below the surface of the skin, in the immediate vicinity of the healed sites. In addition, a dark line of material could be seen underneath the skin directly behind the base of the larger fibre (refer to FIGS. 4 and 5). This almost certainly represented a continuation of the exposed length of hair, and indicated that the follicle producing it was shallowly embedded and at an unusual angle and orientation relative to the local follicles. Both fibres increased in mass and length over the next few weeks, but this was more pronounced in the pigmented fibre which became more obviously stouter and thus morphologically distinct from the local hairs (refer to FIGS. 4 and 5). The finer white fibre was covered by a thin layer (or sac) of dried cells, but otherwise, was quite similar in stature and general appearance to the neighbouring non-induced hairs. Twenty one days after the second set of operations (initiated three months after the first) a fibre (again darker and sturdier than the local hairs) was seen at the sheath-implanted site. Over a further similar time span of three weeks, this solidly pigmented hair grew thicker and became more curved. The site was biopsied on day 42.

Figure 6:
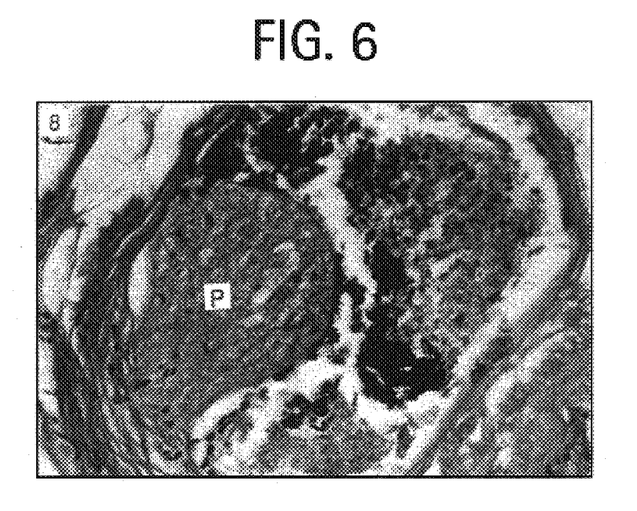
FIG. 6 represents pictorial evidence of a histological section through an end bulb region of an induced follicle, revealing an Alcian blue-positive stained papilla (P).

Histological examination of the sheath-implanted sites confirmed that the two larger follicles which had produced terminal-type fibres externally, had all of the characteristic components. For instance, large oval (Alcian blue-positive) dermal papillae (FIG. 6, legend P) were overlaid by a pigmented epidermal matrix, and follicle-typical concentric tissue layers could also be clearly seen in transverse sections. However, these follicles were quite different from the local vellus population in terms of their: larger size; shallow depth of growth within the skin, and unusual angle of orientation parallel to the skin surface. Such independent and contrasting features strongly suggest that the larger appendages were induced.

Notably, none of the transplanted material was transplanted into an immunoprotected site.

Further smaller follicles were also noted in random positions and arrangements in and around the post-experimental wound sites, and while they too may have been newly formed, their situation could not be interpreted on the basis of the morphological criteria alone.

Evidence in Support of Immunoprivilege as Illustrated by In Situ Hybridisation

Both positive (refer to FIG. 7 which represents pictorial evidence of a lower portion of an induced follicle which can be seen to stain positively following in-situ hybridisation with a Y-chromosome-specific DNA probe, realised via digoxygenin label) and negative (refer to FIG. 8 which represents pictorial evidence of a tissue section acting as a negative control for FIG. 7, and represents female skin that is not stained at all by the digoxygenin-linked Y-chromosome probe) controls stained appropriately to confirm the validity of the protocols basic methodology.

Figure 7:
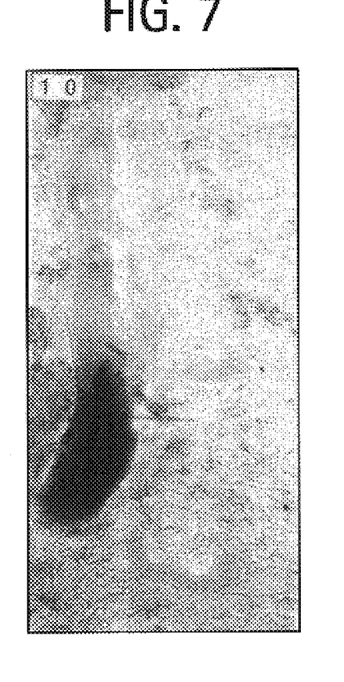
FIG. 7 represents pictorial evidence of a lower portion of an induced follicle which can be seen to stain positively following in situ hybridisation with a Y-chromosome-specific DNA probe, realised via digoxygenin label.
Figure 8:
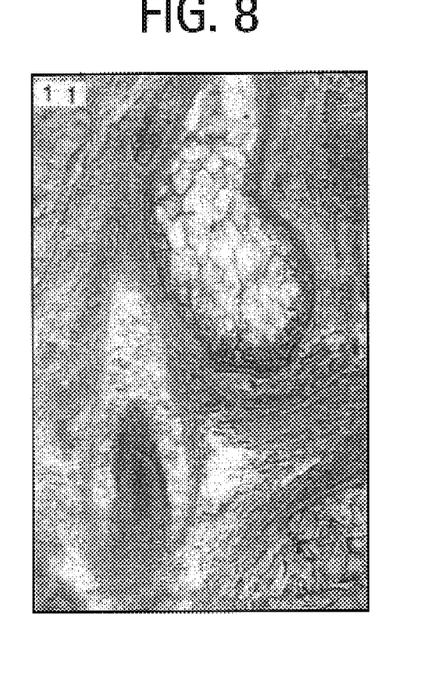
FIG. 8 represents pictorial evidence of a tissue section acting as negative control for FIG. 7 and represents female skin that is not stained at all by the digoxygenin-linked Y-chromosome probe.
Figure 9:
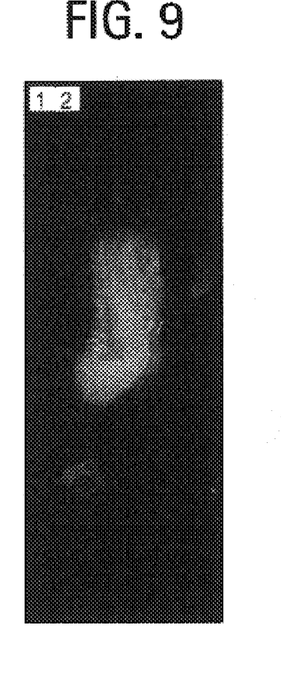
FIG. 9 represents pictorial evidence of a lower portion of an induced follicle stained positively following in situ hybridisation with a Y-chromosome-specific DNA probe, realised via a green fluorophore marker.
Figure 10:
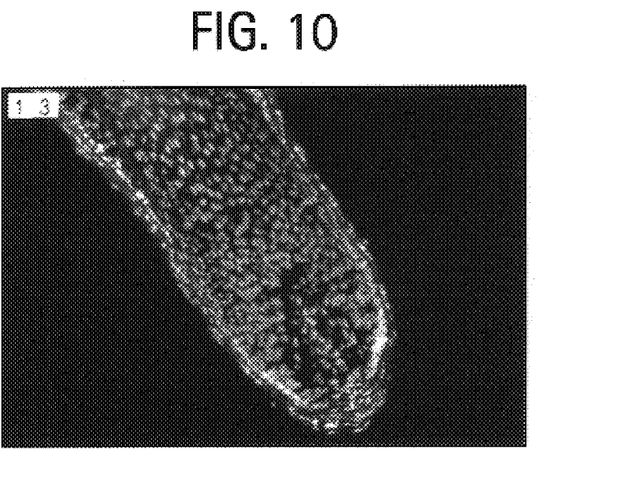
FIG. 10 represents pictorial evidence of a tissue section acting as a positive control for FIG. 9.

In the first set of experimental tissue sections, both of the Y-chromosome-specific DNA probes recognised some of the smaller follicles in the wound sites, as well as the more predictably induced larger ones. Only the lowermost regions of the smaller follicles, in fact, little more than the end bulb regions, repeatedly stained positively with the probes (compare FIGS. 7 and 8), as visualised by either the digoxygenin or the Spectrum green fluorophore to indicate the cells of male origin. Unfortunately, the morphological resolution of the tissue was not adequate to interpret the probes distribution at the level of individual cells, or even tissue layers. Nevertheless, that both the fluorophore, (refer to FIG. 9 compared to FIG. 10) and digoxygenin—(FIG. 7 compared to 8) labelled probe recognised almost identical regions of the follicles tissue as positive, was considered to reinforce the results.

Experimental Evidence in Support of the Ability of Dermal Sheath Cells to Provide Long Term Replacement Skin Dermis Dermal sheath cells were recombined with epidermal cells from hair follicles and grafted, inside a chamber that separated the graft from the surrounding skin cells, onto an animal.

Figure 11:
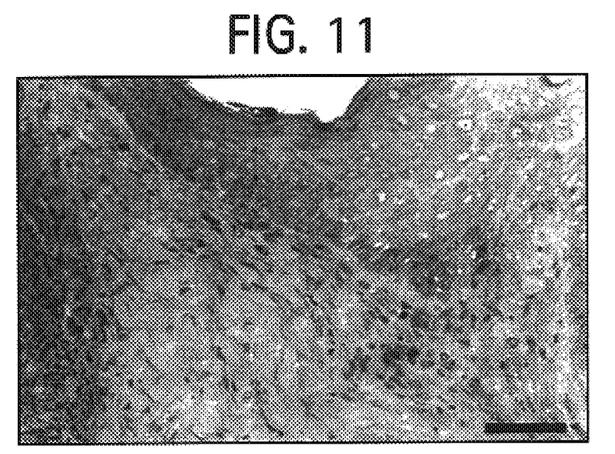
FIG. 11 represents pictorial evidence of a high power magnification view of the side of a long term [24 days] graft.
Figure 12A:
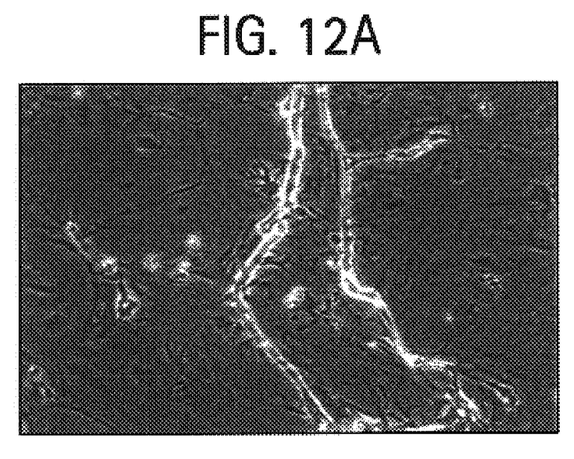
Figure 12B:
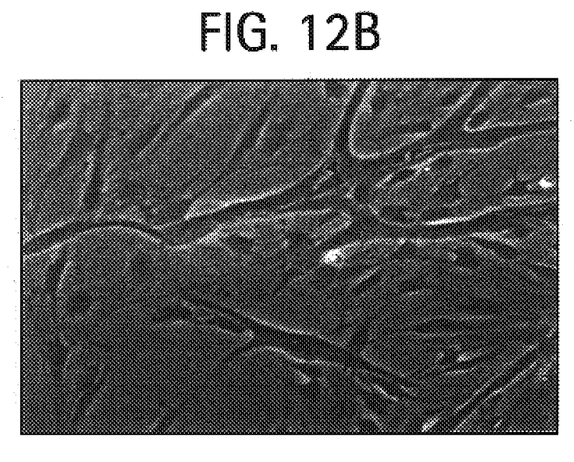
Figure 12C:
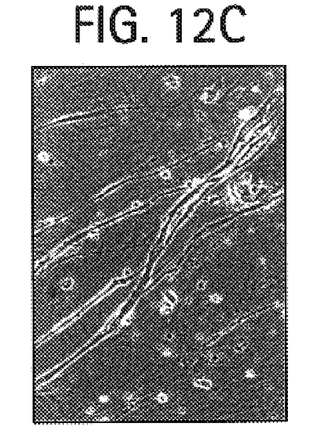
Figure 12D:
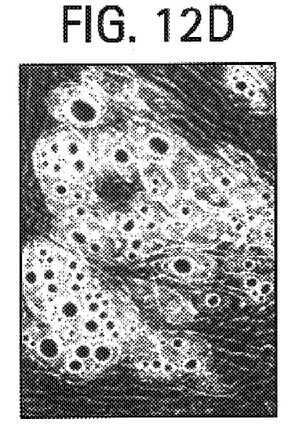
Figure 12E:
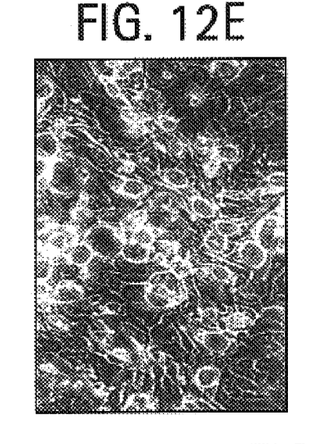
Figure 12F:
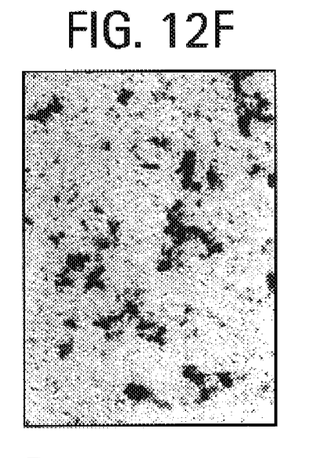
Figure 12G:
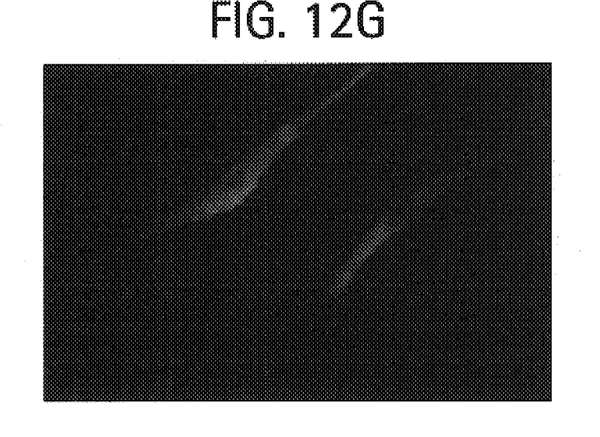
Figure 12H:
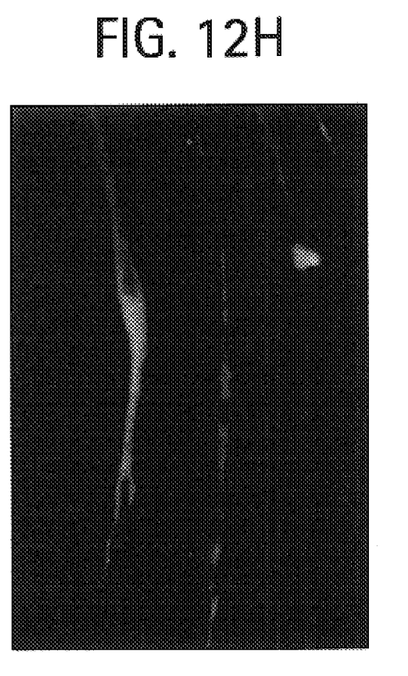
Figure 12I:
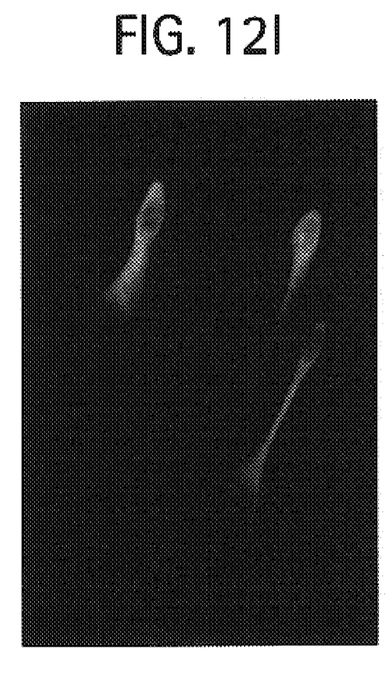

The dermal sheath cells formed a very good dermis with uniform cell density and no sign of abnormal collagen formation. They also interacted with the epidermis to produce a thick epidermal covering. A complete and normal basement membrane was formed between dermal sheath and epidermis. Where the chamber surrounding the graft has been removed, the white block cell infiltrate that has built up outside the graft does not appear to enter the new skin site. Refer to FIG. 11 which represents a high power magnification view of the side of a long term [24 days] graft. The line of dark dense white blood cell infiltrate on the left, has not encroached into the graft site. In the dermis, collagen bundles are structured, dermal cells are regularly distributed and a complete and normal basement membrane is obvious.

Experimental Evidence in Support of Dermal Sheath Cell Stem Cell Potential

FIG. 12 (A–I) represent pictorial evidence of dermal sheath cells capability to differentiate into different mesenchymal cells and hence their stem cell potential. It can be seen that these cells can differentiate into myotubes, adipocytes, chondrocytes and mineral producing bone cells. Further surprising evidence includes hair follicle tissue, obtained from individuals in the 95–105 age range, was found to be viable and capable of acting as a productive source for cell culture initiation. This data supports the hypothesis of the capability of stem cells to differentiate and reproduce remains constant during lifetime (10). Additionally repeated freezing and thawing of primary dermal sheath cells and subsequent cloning did not alter their potential to exhibit at least four different phenotypes despite their prior exposure to adverse conditions.

Experimental Evidence in Support of Dermal Sheath Multipotentiality

Muscle Myotubes

Subpopulations of small spindle-shaped cells were observed both singularly and in various states of fusion (as can also be commonly seen in routinely prepared cultures), some forming long branching, multinucleate myotube-like structures. A proportion of these cells strained positively with myosin, desmin and/or alpha-smooth muscle actin monoclonal antibodies. [There have even been an odd occasion in the past when we have observed spontaneous rhythmic beating, i.e. contractions, of long aggregations of such muscle precursor-type cells in our petri dishes].

Adipocytes

These cells were identified by their distinctive multivesiculate appearance and the fact that the material contained within their vesicles was stained red by Sudan IV, and thus shown to be saturated neutral lipid.

Chondrocytes

Seen as accumulations of rounded cells with pericellular pH 1.0 Alcian Blue positive material which would be chondriotin and keratan sulphate proteoglycans, and lacunae between many of the cells—{interestingly similar cell behaviour is observed when rat dermal sheath cells are mixed with microdissected ear cartlidge in vitro}. This also seems likely to be related to our observations in vivo, when implanted dermal sheath cells appear to stimulate hyperplasia in the normally inactive ear cartilage.

Mineral Producing Bone Cells

These cells were identified by their formation of aggregates in which the matrix appeared mineralised and shined positively for calcium phosphates, after being treated by the von Kossa method.

Further distinctive cell types have also been observed in our dermal sheath cell cultures (including interesting dendritic populations) but as yet these remain inaccurately defined.

Figure 13:
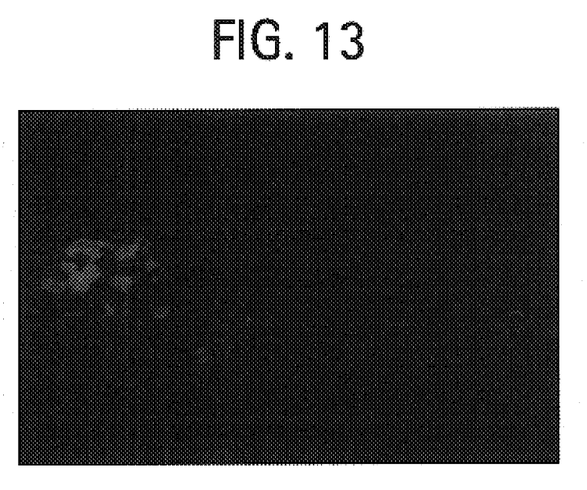
FIG. 13 represents pictorial evidence of skin at the margin of a wound and in which dermal sheath cells have surrounded an isolated follicle in the undamaged tissue away from the main group of labelled cells remote in undamaged tissue.

Experimental Evidence in Support of Dermal Sheath Cells as Substitutes for Fibroblasts in Skin Wounding Fluorescent dye (DiI) labelled dermal sheath cells and fibroblasts were implanted into skin wounds in a collagen gel, dermal sheath cells survived comparably to skin cells over 10 days and were observed to penetrate further into host skin. Dermal sheath cells were also shown to be capable of migration and incorporating themselves into normal skin away from the wound itself (refer to FIG. 13 which represents pictorial evidence of skin at the margin of a wound and in which dermal sheath cells have surrounded an isolated follicle remote in undamaged tissue).

Storage of Dermal Sheath Tissue

Our investigations have shown that dermal sheath tissue and/or cells derived therefrom can be stored long term at low temperatures and yet still, when subjected to appropriate conditions, grow. This clearly has important implications in the storage of wound healing therapeutics, and specifically, the storage of grafts or "living skins" made therefrom.

Moreover, our investigations have also shown that the dermal sheath cells can persist for a long time in culture under conditions of extreme stress. This has important implications for wound healing therapeutics derived from this tissue, since it highlights that it is favourably robust and also that it displays stem cell characteristic durability and viability.

Evidence in Support of Transfected Dermal Sheath Cells

Using the construct containing enhanced green fluorescent protein e-GFP depicted in FIG. 14 obtained by the method outlined in FIG. 15. Two sets of dermal sheath cells were transfected on two separate occasions and were shown to visibly express the GFP by 36 hours (refer to FIG. 16). Ally cells that contained the construct were identified by their fluorescence. Transfection rates were reasonably high, approaching 20% of the cells. Furthermore, the cells remained green for more than 2 weeks. It is our assumption that the cells would survive in vivo if they were put back into humans/other species either at the same or different sites.

In short, not only does dermal sheath tissue and/or cells derived therefrom and/or cells typically closely associated with hair follicles have all the advantageous properties that one might hope to find in a gene therapy system but they also have properties that facilitate the use of the tissue and/or cells derived therefrom in terms of manufacturing and long term storage.

REFERENCES

1. Anderson W. F. (1998). Human gene therapy. Nature 392: 25–30.
2. Mulligan R. C. (1993). The Basic Science of Gene Therapy. Science 260: 926–932.
3. Malkinson, F. D. & Keane, J. T. (1978). Hair matrix kinetics: a selective review. Int J Dermatol. 17, 536–551.
4. Oliver R. F. & Jahoda C. A. B. (1989). The dermal papilla and maintenance of hair growth. In The biology of wool and hair. (ed. G. E. Rogers, P. J. Reis, K. A. Ward, R. C. Marshall), pp.51–67. Cambridge: Cambridge University Press.
5. Reynolds, A. J. and Jahoda, C. A. B. (1991a). Inductive properties of hair follicle cells. In The Molecular and Structural Biology of Hair. Proc. N.Y. Acad. Sci. 624, 226–242.
6. Reynolds, A. J. & Jahoda, C. A. B. (1992). Cultured dermal papilla cells induce follicle formation and hair growth by transdifferentiation of an adult epidermis. Development 115, 587–593.
7. Reynolds, A. J., Lawrence, C. & Jahoda, C. A. B. (1993). Culture of human hair follicle germinative epidermal cells. J. Invest Dermatol. 101, 634–638.
8. Oliver, R. F. (1966). Histological studies of whisker regeneration in the hooded rat. J. Embryol. Exp. Morphol. 16: 231–244.
9. Jahoda, C. A. B., Horne K. A., Mauger, A., Bard S., & Sengel P. (1992). Cellular and extracellular involvement in the regeneration of the rat lower vibrissa follicle. Development 114: 887–897.
10. Haynesworth, S. E, Goldberg, V. M. & Caplan, A. I. (1993). Diminution of the number of mesenchymal stem cells as a cause for skeletal ageing. Chapter 7. In: Musculoskeletal soft-tissue ageing impact on mobility. [Eds. J. A. Buckwater & V. M. Goldberg]. pp 79–87.

What is claimed is:

1. A therapeutic composition, comprising isolated hair follicle dermal sheath tissue and/or a cell derived therefrom comprising at least one selected gene, or functional fragment thereof, and wherein said at least one selected gene, or functional fragment thereof is delivered to a target site when said dermal sheath tissue is part of a gene therapy vehicle.

2. A gene therapy vehicle for delivering at least one selected gene, or functional fragment thereof, to a target site wherein said gene therapy vehicle comprises isolated hair follicle dermal sheath tissue and/or a cell derived therefrom.

3. The therapeutic composition of claim 1, wherein said dermal sheath tissue or cell is derived from the lower portion of a hair follicle.

4. The therapeutic composition of claim 3, wherein said dermal sheath tissue or cell is derived from a lower third of said hair follicle.

5. The therapeutic composition of claim 3, wherein said dermal sheath tissue or said cell is derived from a segment or ring of a combination of follicle/tissue cells.

6. The gene therapy vehicle of claim 2, which is engineered by recombinant techniques so as to include at least one insertion site into which at least one selected gene be placed.

7. The gene therapy vehicle of claim 6, wherein said selected gene is inserted into said gene therapy vehicle so that the expression of said selected gene results in the provision of the corresponding protein product.

8. The gene therapy vehicle of claim 7, wherein said vehicle is provided with multiple insertion sites to carry multiple genes and wherein when said genes are expressed said gene therapy vehicle provides for the delivery of multiple proteins.

9. The gene therapy vehicle of claim 2, further comprising a promoter wherein said selected gene is under the transcriptional control of said promoter.

10. The gene therapy vehicle of claim 9, wherein said promoter is an inducible promoter.

11. The gene therapy vehicle of claim 9, wherein said promoter is a constitutive promoter.

12. A vector comprising the gene therapy vehicle of claim 2 wherein said vector further comprises
  (i) at least one insertion site for at least one selected gene, or functional fragment thereof, and
  (ii) other expression control elements for ensuring that once the vector infects or penetrates said tissue and/or cells of said gene therapy vehicle, expression of said selected gene can take place.

13. A therapeutic composition comprising a carrier and the gene therapy vehicle of claim 2.

14. The therapeutic composition of claim 13, wherein said composition has anti-bacterial properties.

15. The therapeutic composition of claim 13, wherein said composition has anti-septic properties.

16. The therapeutic composition of claim 13, wherein said composition further comprises growth promoting additives.

17. The therapeutic composition of claim 13, wherein said composition further comprises at least one anaesthetic.

18. The therapeutic composition of claim 13, for topical application wherein said therapeutic composition is provided in a suitable carrier solution, gel, cream, or emollient.

19. The therapeutic composition of claim 13, wherein said therapeutic composition comprises a carrier solution as said carrier.

20. A therapeutic appliance comprising the therapeutic composition of claim 13, wherein said carrier is incorporated therein, and/or attached thereto, a plaster or bandage.

21. A gene therapy vehicle for use in delivering a selected gene, or functional fragment thereof, to a given site wherein said gene therapy vehicle comprises hair follicle dermal sheath tissue and/or a cell derived therefrom, which tissue and/or cells comprise heterologous genetic material and which, in vivo, said dermal sheath tissue and/or cell differentiate to provide at least one differentiated tissue type.

22. The gene therapy vehicle of claim 21, which acts as a wound healing system.

23. A wound healing system comprising a matrix material having incorporated therein, and/or attached thereto, the gene therapy vehicle of claim 21.

24. A wound healing system according to claim 23 wherein said matrix material comprises native collagen.

25. The wound healing system of claim 23, wherein said matrix material comprises collagenous gels or lattices constructed from reconstituted collagen.

26. The wound healing system of claim 25, wherein said matrix material comprises components from an extra cellular matrix.

27. A wound healing system according to claim 26 comprising a surgical dressing.

28. The wound healing system of claim 27, for treatment of acute, and/or chronic, and/or minor, and/or severe, wound healing.

29. A wound healing system according to claim 28 for use in the treatment of cartilage repair, and/or bone repair, and/or muscle repair, and/or connective tissue repair, and/or blood vessel repair.

30. A wound healing system according to claim 29 wherein said system comprises a plurality of cell types from a hair follicle.

31. The wound healing system of claim 30, wherein one of said cell types, in addition to said dermal sheath tissue, and/or said cell derived therefrom, comprises dermal papilla tissue.

32. A therapeutic composition according to claim 13 wherein said composition comprises a plurality of cell types from a hair follicle.

33. The therapeutic composition of claim 31, wherein one of said cell types, in addition to said dermal sheath tissue, and/or said cell derived therefrom, comprises dermal papilla tissue.

* * * * *